United States Patent [19]

Osborn, III

[11] Patent Number: 5,383,869
[45] Date of Patent: Jan. 24, 1995

[54] THIN, FLEXIBLE SANITARY NAPKIN

[75] Inventor: Thomas W. Osborn, III, Cincinnati, Ohio

[73] Assignee: The Procter & Gamble Company, Cincinnati, Ohio

[21] Appl. No.: 960,176

[22] Filed: Oct. 8, 1992

Related U.S. Application Data

[63] Continuation of Ser. No. 688,755, Apr. 22, 1991, abandoned, which is a continuation of Ser. No. 570,231, Aug. 20, 1990, Pat. No. 5,009,653, which is a continuation of Ser. No. 293,606, Jan. 4, 1989, Pat. No. 4,950,264, which is a continuation-in-part of Ser. No. 175,559, Mar. 31, 1988, abandoned.

[51] Int. Cl.$^6$ .............................................. A61F 13/15
[52] U.S. Cl. .................................. 604/385.1; 604/358; 604/387
[58] Field of Search ................. 604/368, 378, 385.1, 604/385.2, 358, 387

[56] References Cited

U.S. PATENT DOCUMENTS

| | | | |
|---|---|---|---|
| 3,397,697 | 8/1968 | Rickard | 128/288 |
| 3,455,303 | 7/1969 | Wilson | 128/289 |
| 3,570,491 | 3/1971 | Snelder | 128/290 |
| 3,881,490 | 5/1975 | Whitehead et al. | 128/287 |
| 4,057,061 | 11/1977 | Ishikawa et al. | 128/284 |
| 4,217,901 | 8/1980 | Bradstreet et al. | 604/368 |
| 4,467,012 | 8/1984 | Pedersen et al. | 428/248 |
| 4,500,315 | 2/1985 | Pieniak et al. | 604/379 |
| 4,537,590 | 8/1985 | Pieniak et al. | 604/379 |
| 4,540,454 | 9/1985 | Pieniak et al. | 156/62.2 |
| 4,559,050 | 12/1985 | Iskra | 604/368 |
| 4,560,372 | 12/1985 | Pieniak | 604/369 |
| 4,573,988 | 3/1986 | Pieniak et al. | 604/379 |
| 4,596,567 | 6/1986 | Iskra | 604/368 |
| 4,605,402 | 8/1986 | Iskra | 604/368 |
| 4,610,678 | 9/1986 | Weisman et al. | 604/368 |
| 4,654,038 | 3/1987 | Sakurai | 604/368 |
| 4,654,040 | 3/1987 | Luceri | 604/385 R |
| 4,681,578 | 7/1987 | Anderson et al. | 604/385 R |
| 4,701,178 | 10/1987 | Glaug et al. | 604/387 |
| 4,846,829 | 7/1989 | Lloyd | 604/389 |
| 4,950,264 | 8/1990 | Osborn III | 604/385.1 |
| 5,009,653 | 4/1991 | Osborn III | 604/385.1 |

FOREIGN PATENT DOCUMENTS 0215417 3/1987 European Pat. Off. ..... A61L 15/00

OTHER PUBLICATIONS

D. C. Schmitz, Laboratory Notebook WP2374, pp. 21-27.

T. W. Osborn, Compilation of Data from Laboratory Notebook WP2374.

Primary Examiner—Randall L. Green
Assistant Examiner—Rob Clarke
Attorney, Agent, or Firm—Larry L. Huston

[57] ABSTRACT

In accordance with the present invention, a sanitary napkin having a body surface and a garment surface and being comprised of an absorbent means underlayed by a liquid barrier means, wherein the sanitary napkin is relatively highly flexible and has a capacity great enough to handle medium to high menstrual flows, is provided. In a preferred embodiment, the sanitary napkin comprises, from the body surface down, an apertured formed film topsheet, an apertured nonwoven wipe acquisition sheet, a wet-laid tissue, a superabsorbent core, and a barrier sheet. Preferably, the central width of the absorbents is at least about 6.5 centimeters and the caliper of the napkin as a whole is less than about 2.6 millimeters. In a preferred embodiment, the napkin has laterally extending flaps which drape over the edges of the wearer's panties in the crotch and are attachable to the garment side of the wearer's panties.

7 Claims, 2 Drawing Sheets

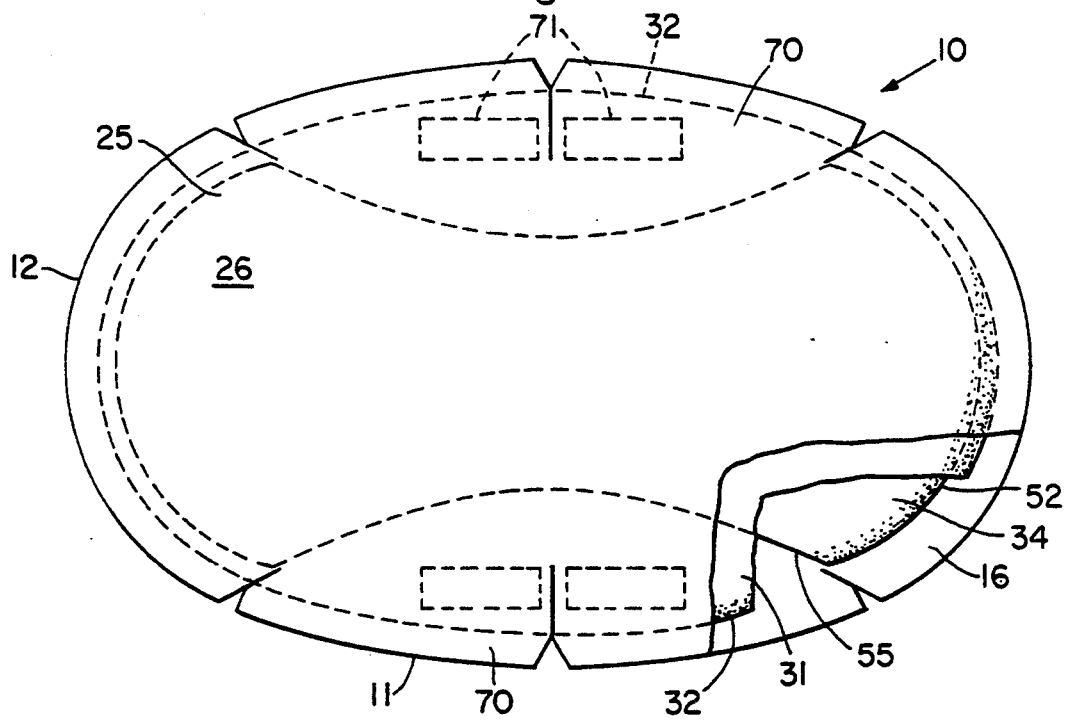
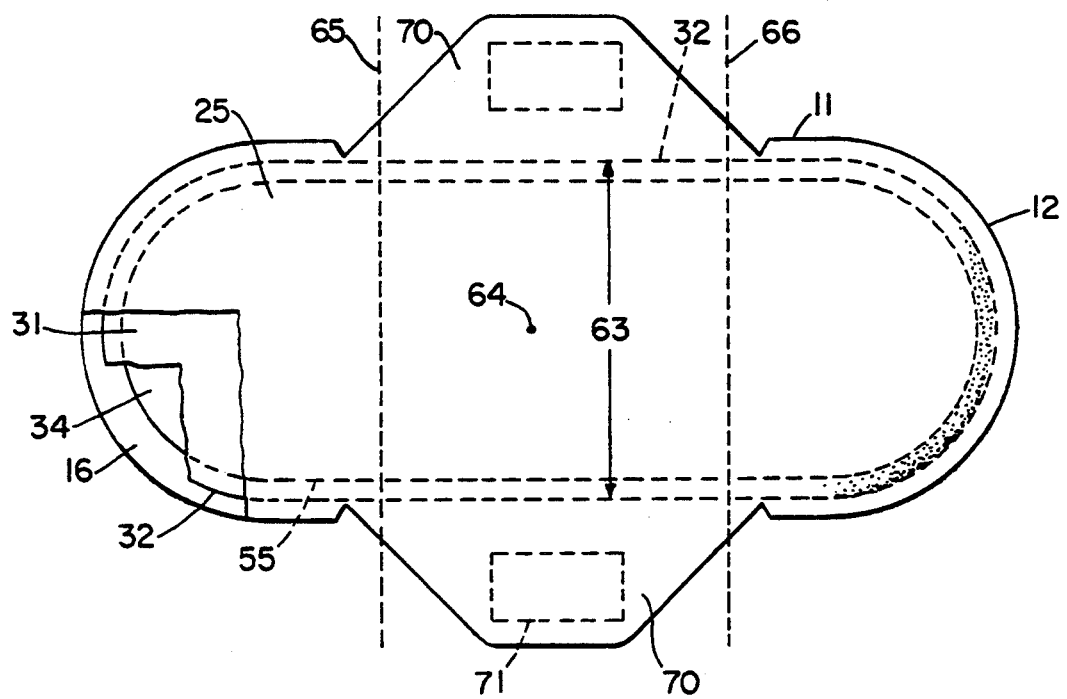

THIN, FLEXIBLE SANITARY NAPKIN

This is a continuation of application Ser. No. 07/688,755, filed on Apr. 22, 1991 now abandoned, which is a continuation of Ser. No. 07/293,606 now U.S. Pat. No. 4,950,264 which is a continuation-in-part of Ser. No. 07/175,559 filed Mar. 31, 1988, now abandoned.

BACKGROUND OF THE INVENTION

1. Field of the Invention

The present invention relates to female sanitary napkins. Particularly, the present invention concerns thin, flexible sanitary napkins offering enhanced fit and comfort through a construction which promotes a continuously self-conforming anatomical cooperation of the sanitary napkin to the wearer to yield a highly effective absorbent device.

2. BACKGROUND ART

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", which patent issued to Weigner et al. on Nov. 1, 1983, and U.S. Pat. No. 4,413,986, entitled "Tampon Assembly With Means For Sterile Insertion", which patent issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", which patent issued to Arone on Sep. 7, 1937, and U.S. Pat. No. 3,905,372, entitled "Feminine Hygiene Protective Shield", which patent issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", which patent issued to Jacks on Dec. 15, 1953, and U.S. Pat. No. 4,631,062, entitled "Labial Sanitary Pad", which patent issued to Lassen et al. on Dec. 23, 1986.

With respect to sanitary napkins, at least two general classes pertinent to the present invention exist. One such class is for the absorption of medium to high menstrual flows. These sanitary napkins offer a fairly high absorptive capacity. Absorptive capacity is commonly achieved by providing the napkin with a fairly thick and bulky absorbent member, commonly fluff pulp. Sanitary napkins of this class are disclosed in U.S. Pat. No. 3,294,091, entitled "Sanitary Napkin", which patent issued to Morse on Dec. 27, 1966, U.S. Pat. No. 4,654,040, entitled "Smooth-Edged Contoured Sanitary Napkin", which patent issued to Luceri on Mar. 31, 1987, and U.S. Pat. No. 4,687,478, entitled "Sanitary Napkin With Flaps", which patent issued to Van Tilburg on Aug. 18, 1987. Such sanitary napkins theoretically have a high absorptive capacity, however, when the sanitary napkin is worn and subjected to the compressive forces of the wearer's thighs and pudendal region, the fluff pulp core simply compacts or bunches into an arbitrary, but generally rope-like shape. Such napkins commonly shift from their original placement so that after only a short wearing time, the napkin might only partially, if at all, be beneath the wearer's vaginal orifice or vestibule. Thus, in use, these sanitary napkins sometimes offer very little absorption. Further, the rolling and twisting of these napkins may create soiling on the wearer's panties and skin surfaces. In addition, the bulkiness of these napkins causes a high degree of wearing awareness and may make them quite obtrusive when worn with tight fitting slacks, body suits or bathing suits.

A second class of sanitary napkins are intended for light or low menstrual flows and are commonly referred to as panty liners or panty shields. Sanitary napkins of this type are disclosed in U.S. Pat. No. 4,681,578, entitled "Pantiliner With Ventilation Areas", which patent issued to Anderson and Brandt on Jul. 21, 1987. Sanitary napkins of this class, as a group, are thinner, somewhat more flexible and generally more comfortable than those of the first class, however, they lack the absorptive capacity of the napkins of the first class.

Therefore, there exists a real consumer need for a sanitary napkin which is thin and flexible, thereby offering enhanced fit and comfort, yet having a fluid capacity great enough for use with medium to high menstrual flows thereby allaying consumer fears of leakage and staining.

Therefore, it is an object of the present invention to provide a sanitary napkin which is thin and flexible and which is absorbent enough to absorb and contain medium to high menstrual flows.

It is an additional object of the present invention to provide a sanitary napkin which will closely conform to the various anatomical shapes of the female urogenital and buttocks region.

It is an additional object of the present invention to provide a sanitary napkin which offers enhanced fit and comfort and a low degree of wearing awareness.

It is an additional object of the present invention to provide a thin and flexible sanitary napkin having laterally extending flaps configured to drape over the side edges of the wearer's panties in the crotch portion thus being disposed between the side edges of the wearer's panties in the crotch portion and the wearer's thighs.

It is an additional object of the present invention to provide the laterally extending flaps with an attachment means on their garment facing surface so that the flaps can wrap around the side edges of the wearer's panties in the crotch portion and be attached to the garment facing side of the wearer's panties in order to provide protection from soiling and so as to keep the napkin properly positioned in the wearer's panties.

These and other objects of the present invention will be more readily apparent when considered in reference to the following description and when taken in conjunction with the accompanying drawings.

SUMMARY OF THE INVENTION

In accordance with the present invention, a sanitary napkin having a body surface and a garment surface and being comprised of an absorbent means underlayed by a liquid barrier means, wherein the sanitary napkin is relatively highly flexible and has a capacity great enough to handle medium to high menstrual flows, is provided. In a preferred embodiment, the sanitary napkin comprises, from the body surface down, an apertured formed film topsheet, an apertured nonwoven wipe acquisition sheet, a wet-laid tissue, a superabsorbent core, and a barrier sheet. Preferably, the central width of the absorbents is at least about 7.0 centimeters and the caliper of the napkin as a whole is less than about 2.5 millimeters. In a preferred embodiment, the napkin has laterally extending flaps which drape over the edges of the wearer's panties in the crotch and are attachable to the garment side of the wearer's panties.

BRIEF DESCRIPTION OF THE DRAWINGS

FIG. 4 is a top plan view of an alternatively preferred sanitary napkin embodiment of the present invention with portions being torn away to show underlying structure.

FIG. 5 is a top plan view of another alternatively preferred sanitary napkin embodiment of the present invention with portions being torn away to show underlying structure.

DETAILED DESCRIPTION OF PREFERRED EMBODIMENTS

The present invention relates to female sanitary napkins and in particular to sanitary napkins which are thin and flexible and offer enhanced fit, comfort, and containment.

As used herein, the term "sanitary napkin" refers to an article which is worn by females adjacent to the pudendal region and which is intended to absorb and contain the various exudates which are discharged from the body (e.g., blood, menses and urine) and which is intended to be discarded after a single use (i.e., it is not intended to be laundered or otherwise restored or reused). Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
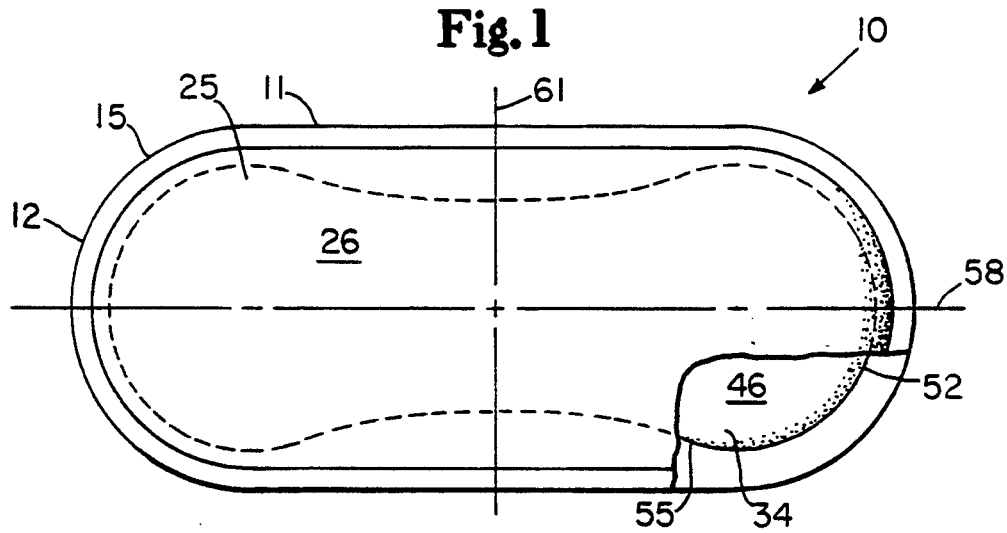
FIG. 1 is a top plan view of a preferred sanitary napkin embodiment of the present invention with portions being torn away to show underlying structure.
Figure 2:
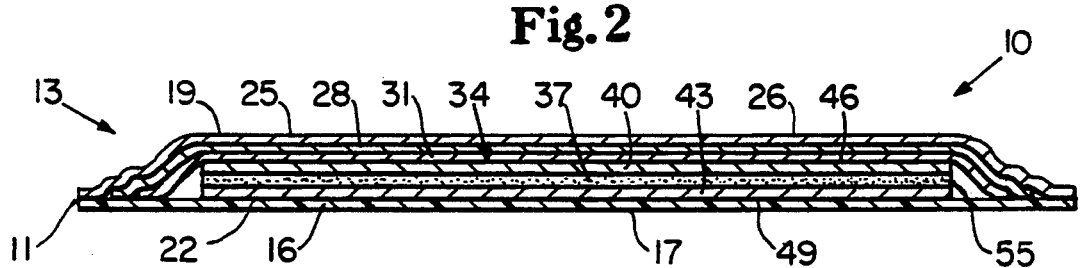
FIG. 2 is a lateral cross-sectional view of the preferred sanitary napkin embodiment shown in FIG. 1 taken along line 2—2 of FIG. 1.

A preferred embodiment of a sanitary napkin 10 of the present invention is shown in FIGS. 1 and 2. As can be seen in FIGS. 1 and 2, a preferred sanitary napkin 10 basically comprises an absorbent means 13 and a liquid impermeable barrier means 16. The absorbent means 13 may be any means which is generally compressible, conformable, non-irritating to the wearer's skin and capable of absorbing and containing body exudates such as menses, blood and urine. Preferably, the absorbent means 13 maintains integrity when wetted, in use. The absorbent means 13 has a first major surface 19 and a second major surface 22. The barrier means 16 is adjacent the second major surface 22 of the absorbent means 13. The barrier means 16 may be any means which is flexible and liquid impervious and which prevents the exudates absorbed and contained in the absorbent means 13 from wetting articles which contact the sanitary napkin 10 such as panties.

In the preferred embodiment shown in FIGS. 1 and 2, the absorbent means 13 is comprised of a liquid permeable topsheet 25, a liquid permeable wipe acquisition sheet 28, a wet-laid tissue sheet 31 and an absorbent core 34. In the preferred embodiment shown in FIGS. 1 and 2, the barrier means 16 is a barrier sheet. The absorbent core 34 is comprised of hydrogel-forming material 37 disposed between two air-laid tissue sheets 40 and 43. The sanitary napkin 10 has side edges 11 and end edges 12 which together form the periphery 15 of the sanitary napkin 10. The sanitary napkin 10 has a body surface 26 which is generally defined by the topsheet 25 and a garment surface 17 which is generally defined by the barrier sheet 16.

Looking at some of the elements of the sanitary napkin 10 more specifically, the absorbent core 34 may be any means which is generally compressible, conformable, non-irritating to the wearer's skin and capable of absorbing and containing body exudates. The absorbent core 34 has a first major surface 46, a second major surface 49, a pair of end edges 52 and a pair of side edges 55. The absorbent core 34 may be manufactured in a wide variety of sizes and shapes (e.g., rectangular, hourglass, etc.). A preferred shape of the absorbent core 34 is the dogbone shape shown in FIG. 1. This preferred absorbent core 34 is about 22.0 centimeters long (longitudinal dimension along the longitudinal centerline 58), about 7.0 centimeters wide across its midportion (lateral dimension along the lateral centerline 61) and about 8.0 centimeters wide across its widest portion (lateral dimension). The absorbent core 34 is symmetrically configured for ease of manufacture and so that no conscious effort is required by the wearer to properly place the napkin 10 in the direction it should be worn. The midportion is configured to basically conform to the wearer's thighs and to the thinner crotch portion of the wearer's panties so as to prevent excessive bunching. The size of the absorbent core 34 may be varied to accommodate wearers ranging in size and also ranging in the expected amount of exudate fluid volume. The absorbent core 34 may be attached over the core's first or second major surfaces 46 and 49, respectively, to adjacent members such as the topsheet 25 and barrier sheet 16 by any of the means well known in the art, such as by spray-gluing or lines or spots of adhesive. Such attachment facilitates integrity and recoverability of the absorbent materials in use so as to maintain an optimum degree of absorbency. Preferably, the absorbent core 34 has a wet-tensile strength in the cross-direction of at least about 100.0 grams per centimeter. Wet tensile strength is determinable by ASTM Standard D 829-49.

The absorbent core 34 may be manufactured from a wide variety of liquid absorbent materials commonly used in disposable sanitary napkins, diapers, and other absorbent articles. Examples of suitable absorbent materials include comminuted wood pulp which is generally referred to as airfelt, creped cellulose wadding, absorbent foams, absorbent sponges, synthetic staple fibers, polymeric fibers, hydrogel-forming polymer gelling agents, or any equivalent materials or combinations of materials. A particularly preferred absorbent material are polymeric gelling agents. Polymeric gelling agents are those materials which, upon contact with fluids (i.e., liquids) such as water or body fluids, imbibe such fluids and thereby form hydrogels. In this manner, fluid discharged into the absorbent core 34 can be acquired and held by the polymeric gelling agent, thereby providing the articles herein with enhanced absorbent capacity and/or improved fluid retention performance.

The polymeric gelling agent which is employed in the absorbent core 34 will generally comprise particles of a substantially water-insoluble, slightly cross-linked, partially neutralized, hydrogel-forming polymer material. Such polymer materials can be prepared from polymerizable, unsaturated, acid-containing monomers. Suitable unsaturated acidic monomers for use in preparing the polymeric gelling agents used in this invention include those listed in U.S. Pat. No. 4,654,039, entitled "Hydrogel-Forming Polymer Compositions For Use In Absorbent Structures", which issued to Brandt, Goldman and Inglin on Mar. 31, 1987, and which patent is incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agent the polymeric component formed from unsaturated, acid-containing monomers may be grafted onto other types of polymer moieties such as starch or cellulose. Polyacrylate grafted starch materials of this type are especially preferred for use herein.

Preferred polymer gelling agents which can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric gelling agents used in the absorbent core 34 herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in U.S. Pat. No. 4,076,663, which patent issued to Masuda et al. on Feb. 28, 1978, and which patent is incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5.0 mole percent of the resulting hydrogel-forming polymer material. More preferably, the cross-linking agent will comprise from about 0.01 mole percent to 3.0 mole percent of the hydrogel-forming polymeric gelling agent used herein.

The slightly cross-linked, hydrogel-forming polymeric gelling agents which may be used in the articles of the present invention are generally employed in their partially neutralized form. For purposes of this invention, such materials are considered partially neutralized when at least 25.0 mole percent, and preferably at least 50.0 mole percent of monomers used to form the polymer are acid group-containing monomers which have been neutralized with a salt-forming cation. Suitable salt-forming cations include alkali metal, ammonium, substituted ammonium, and amines. This percentage of the total monomer utilized which are neutralized acid group-containing monomers is referred to herein as the "degree of neutralization."

The polymeric gelling agent materials used in the absorbent articles herein must have a relatively high capacity for imbibing fluids encountered in such articles. The absorbent capacity of these materials can be quantified by referencing the "gel volume" of the polymeric gelling agents which are to be selected for use in the present invention.

For purposes of this invention, gel volume can be defined in terms of the amount of synthetic urine absorbed by any given polymeric gelling agent and is specified as grams of synthetic urine per gram of polymeric gelling agent. Gel volume in synthetic urine can be determined by forming a suspension of about 0.1–0.2 parts of dried polymeric gelling agent to be tested with about 20 parts of synthetic urine. This suspension is maintained at ambient temperature under gentle stirring for a time sufficient, e.g., about 1 hour, for swelling equilibrium to be attained. The gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension.

The gel volume of the gelling agents used in the absorbent core 34 herein will generally be at least about 20.0 grams of synthetic urine per gram of polymeric gelling agent. More preferably, the gel volume of the materials employed will range from about 20.0 to about 60.0, most preferably from about 22.0 to about 35.0 grams of synthetic urine per gram of polymeric gelling agent.

Within the webs which form the layers of the absorbent core 34, the particles of the polymeric gelling agent should be thoroughly dispersed but may or may not be uniformly distributed. In particular, there may be regions or zones of the core layers which have higher concentrations of gelling agent particles than do other regions or zones of the layers.

In a preferred embodiment, the sanitary napkin 10 of the present invention will have a hydrogel-forming polymeric gelling agent distributed throughout at least about 17.0 square centimeters of the napkin, more preferably throughout at least about 50.0 square centimeters of the napkin, and most preferably throughout at least about 100.0 square centimeters of the napkin. Preferably, the hydrogel-forming polymeric gelling agent will be distributed in an amount of from about 0.001 grams per square centimeter to about 0.009 grams per square centimeter, more preferably of from about 0.003 grams per square centimeter to about 0.008 grams per square centimeter, and most preferably from about 0.004 grams per square centimeter to about 0.007 grams per square centimeter. Preferably, the absorbent core 34 will contain from about 5.0% to about 85.0% by weight of hydrogel-forming polymeric gelling agent, more preferably from about 10.0% to about 70.0%, and most preferably from about 15.0% to about 55.0%.

In the preferred embodiment shown in FIG. 2, the absorbent core 34 is a laminate comprised of a layer of superabsorbent polymer material 37 disposed between two air-laid tissues 40 and 43. A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which patent issued to Pedersen et al. on Aug. 21, 1984, and U.S. Pat. No. 4,260,443, entitled "Laminated Absorbent Process", which patent issued to Lindsay et al. on Apr. 7, 1981, and which patents are incorporated herein by reference. The WATER-LOCK L-535 has a hydrogel polymer loading of 0.005 grams per square centimeter, however, loadings of 0.001–0.009 grams per square centimeter have been found acceptable. The first and second tissue layers 40 and 43 provide containment of the superabsorbent polymer material 37, improve lateral wicking of the absorbed exudates throughout the absorbent core 34 and provide a degree of absorbency. In the case of non-particulate hydrogel-forming polymer gelling agents which can be formed into fibrous sheets, foams or films, the non-particulate gelling agent may comprise from about 15% to about 100% by weight of the absorbent core 34, more preferably of from about 40% to about 100%, and most preferably of from about 60% to about 100%. The basis weight of such non-particulate superabsorbents may be from about 0.002 to about 0.028 grams per square centimeter, more preferably of from about 0.003 to about 0.018, and most preferably of from about 0.004 to about 0.010. Two suitable and commercially available non-particulate absorbent materials for the absorbent core 34 are a double layer acrylic fibrous material available under the tradename Lanseal F from the Choli Company, LTD., of Higashi, Osaka Japan and a carboxymethylcellulose fibrous material available under the tradename Aqualon C from Hercules, Inc. of Wilmington, Del.

The total absorbent capacity of the absorbent core 34 should be compatible with the design exudate loading for the intended use of the sanitary napkin 10. Further, the absorbent capacity of the absorbent core 34 may be varied to accommodate wearers ranging in the expected amount of exudate fluid volume. For instance, a different absorbent capacity may be utilized for sanitary napkins intended for daytime use as compared with those intended for nighttime use, or for sanitary napkins intended for use by teenage females as compared with those intended for use by more mature women.

It should be noted that the scope of the present invention is not intended to extend to sanitary napkins which are void of any superabsorbent material and which have a central absorbent member overlayed solely by nonwoven materials, wherein the nonwoven materials have caliper of less than 0.50 millimeters, as determined by the caliper test, as later defined.

Superimposed over the absorbent core 34 and extending about 3.0 millimeters beyond the edges 52 and 55 of the absorbent core 34 is the wet-laid tissue 31. The wet-laid tissue 31 is liquid permeable. A satisfactory wet-laid tissue 31 has a basis weight of about 15.8 grams per square meter and an air permeability of about 30.5 cubic meters per minute per square meter at a pressure differential of about 12.8 millimeters of water. Preferably, the wet-laid tissue 31 maintains integrity when wetted, in use. The wet-laid tissue 31 preferably has a wet tensile strength in the cross-direction of at least about 15.0 grams per centimeter. Suitable tissues 31 and their manufacture are disclosed in U.S. Pat. No. 3,301,746, entitled "Process For Forming Absorbent Paper By Imprinting A Fabric Knuckle Pattern Thereon Prior To Drying And Paper Thereof", which patent issued to Sanford and Sisson on Jan. 31, 1967, and which patent is incorporated herein by reference. In a preferred embodiment, those parts of the wet-laid tissue 31 which extend beyond the edges 52 and 55 of the absorbent core 34 are associated with the barrier sheet 16. The wet-laid tissue 31 may be associated with the barrier sheet 16 by attachment means as are well known in the art such as by spray-gluing or lines or spots of adhesive. The wet-laid tissue 16 serves a number of purposes. The tissue 31 serves to confine any loose superabsorbent material 37 between the tissue 31 and the barrier sheet 16 thereby preventing the superabsorbent material 37 from coming in contact with the wearer's skin. Also, the tissue 31 improves lateral wicking of the absorbed exudates over the absorbent core 34 thereby providing a more even distribution of the exudates throughout the absorbent core 34. Further, the tissue 31 provides some degree of absorbency and further inhibits exudates which have reached and been absorbed by the absorbent core 34 from rewetting the wearer's skin.

Superimposed over the wet-laid tissue 31 is a liquid permeable wipe acquisition sheet 28. In a preferred embodiment, the wipe acquisition sheet 28 is a nonwoven sheet. In the preferred embodiment shown in FIG. 2, the sheet 28 is a spunlaced 70%/30% rayon/polyester fiber sheet. Spunlaced fabrics of this type are manufactured by E. I. DuPont Nemours & Company of Wilmington, Del., and are made available under the tradename "SONTARA" (SONTARA registered TM by E. I. DuPont Nemours & Company). These fabrics are available in a number of suitable styles, however, Style 8407 in its apertured form, having a basis weight of 0.005 grams per square centimeter and a thickness of about 0.04 millimeters, is preferred. The wipe acquisition sheet 28 extends beyond the edges of the wet-laid tissue 31 where it too is associated with the barrier sheet 16. The wipe acquisition sheet 28 greatly improves lateral wicking of exudates over the absorbent core 34 thereby providing a more even distribution of the exudates throughout the absorbent core 34. The lateral wicking of the wipe acquisition sheet 28 is important for the following reason. Many bulky prior art sanitary napkins rely on a high degree of vertical absorption at the point where exudates are initially deposited. In other words, because the absorbent cores of these napkins are fairly thick, they can absorb a high degree of exudates throughout their thickness while utilizing only a small degree of their surface area or lateral absorption capability. However, the relatively thin napkins 10 of the present invention have a comparatively small degree of vertical absorption. Therefore, for a relatively large amount of exudates to be absorbed, a wipe acquisition sheet 28 which can laterally disperse the exudates over a large surface area of the absorbent core 34 where the exudates can better and faster be vertically absorbed is highly desirable. Further, the wipe acquisition sheet 28 provides a fairly high degree of initial absorption during the time interval between the time exudates are deposited onto the topsheet 25 and the time they are absorbed by the absorbent core 34. This property will be more specifically described later.

Superimposed over the wipe acquisition sheet 28 is the liquid permeable topsheet 25. In a preferred embodiment, the topsheet 25 is associated with the wipe acquisition sheet 28 by spray-gluing the topsheet 25 to the surface of the wipe acquisition sheet 28. The topsheet 25 is compliant, soft feeling, and non-irritating to the wearer's skin. Further, the topsheet 25 is liquid previous, permitting liquid to readily transfer through its thickness. A suitable topsheet 25 may be manufactured from a wide range of materials such as polymeric materials, formed thermoplastic films, apertured plastic films, porous foams, reticulated foams, natural fibers (e.g., wood or cotton fibers), synthetic fibers (e.g., polyester or polypropylene fibers) or from a combination of natural and synthetic fibers, with apertured formed films being preferred. Formed films are preferred for the topsheet 25 because they are pervious to liquids and yet non-absorbent. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structure Having Tapered Capillaries", which patent issued to Thompson on Dec. 30, 1975, U.S. Pat. No. 4,324,246, entitled "Disposable Absorbent Article Having A Stain Resistant Topsheet", which patent issued to Mullane and Smith on Apr. 13, 1982, U.S. Pat. No. 4,342,314, entitled "Resilient Plastic Web Exhibiting Fiber-Like Properties", which patent issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which patent issued to Ahr, Louis, Mullane, and Ouellete on Jul. 31, 1984, all of which patents are incorporated herein by reference.

In a preferred embodiment of the present invention, the body surface 26 of the topsheet 25 is hydrophilic. The hydrophilic body surface 26 helps liquid to transfer through the topsheet 25 faster than if the body surface 26 was not hydrophilic. This diminishes the likelihood that menstrual fluid will flow off the topsheet 25 rather than being absorbed by the absorbent core 34. In a preferred embodiment, the body surface 26 of the topsheet 25 is made hydrophilic by treating the body surface 26 with a surfactant. It is preferred that the surfactant be substantially evenly and completely distributed throughout the body surface 26 of the topsheet 25. This can be accomplished by any of the common techniques well known to those skilled in the art. For example, the surfactant can be applied to the topsheet 25 by spraying, by padding, or by the use of transfer rolls. Further, the surfactant can be incorporated into the polymeric materials of a formed film topsheet or between or within the fibers of a nonwoven topsheet.

The barrier means 16 is adjacent the second major surface 22 of the absorbent means 13. In a preferred embodiment, the absorbent means 13 may be affixed over the second major surface 22 of the absorbent means 13 to the barrier means 16. Any of the common techniques well known in the art, such as spray-gluing or lines or spots of adhesive may be used for this purpose. The barrier means 16 generally defines the garment surface 17 of the sanitary napkin 10. The barrier means 16 may be any means which is impervious to liquids and which prevents exudates absorbed and contained in the absorbent means 13 from soiling articles, such as panties, which come in contact with the garment surface 17 of the sanitary napkin 10. In the preferred embodiment of the sanitary napkin 10 illustrated in FIGS. 1 and 2, the barrier means 16 is a barrier sheet manufactured from a thin plastic film. Other flexible liquid impervious materials may also be used. Preferably, the barrier sheet 16 is a polyethylene film having a thickness of from about 0.012 millimeter to about 0.051 millimeter. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The barrier sheet 16 is preferably embossed and/or matte finished to provide a more clothlike appearance. Further, the barrier sheet 16 may permit vapors to escape from the absorbent means 13 while still preventing exudates from passing through the barrier sheet 16.

Preferably, the topsheet 25 and the barrier sheet 16 have length and width dimensions generally larger than the absorbent core 34 so that they extend beyond the edges 52 and 55 of the absorbent core 34 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. The extension of the topsheet 25 and/or the barrier sheet 16 beyond the core end edges 52 and the core side edges 55 of the absorbent core 34 form the end edges 11 and the side edges 12, respectively, of the sanitary napkin 10. In a preferred embodiment, the barrier sheet 16 and the topsheet 25 have an elliptical shape and extend beyond the absorbent core 34 a distance of at least about 1.0 centimeter where they are joined directly to each other by attachment means as are well known in the art. The attachment means may be, for example, a uniform continuous layer of adhesive a patterned layer of adhesive, or an array of separate lines or spots of adhesives.

The sanitary napkin 10 of the present invention has a low flexure-resistance. Thus, the sanitary napkin 10 of the present invention is highly flexible and conforms very well to the various shapes of the female urogenital region. Preferably, the sanitary napkin 10 of the present invention has a flexure-resistance of less than about 250.0 grams, more preferably less than about 175.0 grams and most preferably less than about 130.0 grams.

The flexure-resistance of a sanitary napkin is measured by peak bending stiffness. Peak bending stiffness is determined by a test which is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexure-resistance, simultaneously averaging stiffness in all directions.

APPARATUS

The apparatus necessary for the CIRCULAR BEND PROCEDURE is a modified Circular Bend Stiffness Tester, having the following parts:

A smooth-polished steel plate platform which is 102.0 × 102.0 × 6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice.

A force-measurement gauge and more specifically an Instron inverted compression load cell. The load cell has a load range of from about 0.0 to about 2000.0 grams.

An actuator, and more specifically the Instron Model No. 1122 having an inverted compression load cell. The Instron 1122 is made by the Instron Engineering Corporation, Canton, Mass.

NUMBER AND PREPARATION OF SPECIMENS

In order to perform the procedure for this test, as explained below, five representative sanitary napkins are necessary. From one of the five napkins to be tested, some number "Y" of 37.5×37.5 millimeter test specimens are cut. Specimens having portions in which a topsheet is joined directly to a barrier sheet or which are a laminate of a topsheet, two or less tissue sheets and a barrier sheet, should not be tested. The reason that these specimens are not tested is due to the realization that prior art napkins exist in which a topsheet is joined to a barrier sheet beyond the edges of an absorbent core in the periphery of the napkin, such portions of which are highly flexible. However, the present invention is more concerned with the overall flexibility of the sanitary napkin and not merely the peripheral portions thereof and, therefore, the flexibility of the present invention is more concerned with the flexibility of the significant absorbent portions of the sanitary napkin. If any of these significant absorbent portions of the sanitary napkin meet the parameters of this test, then the sanitary napkin satisfies the test. Therefore, a number of different specimens should be tested from each sanitary napkin. Certainly, the structurally most flexible portion of the sanitary napkin should be tested, excluding those portions excluded above. The test specimens should not be folded or bent by the test person, and the handling of specimens must be kept to a minimum and to the edges to avoid affecting flexural-resistance properties. From the four remaining sanitary napkins, an equal number "Y" of 37.5×37.5 millimeter specimens, identical to the specimens cut from the first napkin, are cut. Thus, the test person should have "Y" number of sets of five identical specimens.

PROCEDURE

The procedure for the CIRCULAR BEND PROCEDURE is as follows. The specimens are conditioned by leaving them in a room which is 21°±1° C. and 50±2% relative humidity for a period of two hours. The test plate is leveled. The plunger speed is set at 50.0 centimeters per minute per full stroke length. A specimen is centered on the orifice platform below the plunger such that the body surface 26 of the specimen is facing the plunger and the garment surface 17 of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

CALCULATIONS

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the "Y" sets tested. Remember, if any of the significantly absorbent portions of the sanitary napkin have the requisite flexure-resistance, then the napkin satisfies the parameters of this test. Therefore, the flexure-resistance for a particularly designed sanitary napkin is the greatest of these average peak bending stiffnesses.

Figure 3:
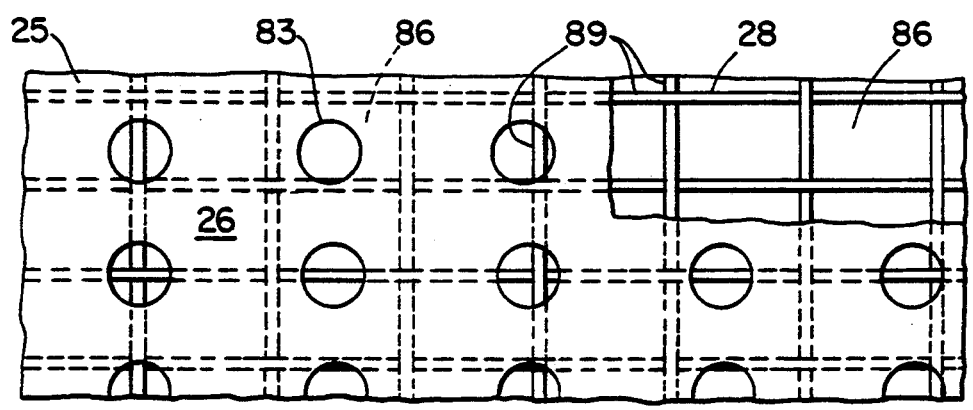
FIG. 3 is a top plan view of a preferred topsheet and wipe acquisition sheet laminate with portions of the topsheet being torn away to show underlying structure.

As alluded to earlier, the combination of topsheet 25 and wipe acquisition sheet 28 imparts some beneficial properties to the sanitary napkin 10. In particular, the combination of an apertured formed film topsheet 25 superimposed over an apertured nonwoven wipe acquisition sheet 28 is beneficial. A preferred wipe acquisition sheet 28 is the previously described SONTARA 8407. An enlarged depiction of such an arrangement is shown in FIG. 3. Such a combination is even more beneficial when the nonwoven wipe acquisition sheet 28 is formed or positioned such that no fiber bundles 89 of the sheet 28 are beneath some of the apertures 83 of the formed film topsheet 25 (i.e., the apertures in the two sheets 25 and 28 are aligned) while beneath other apertures 83 of the formed film topsheet 25 fiber bundles 89 of the nonwoven sheet 28 are present (i.e., apertures in the two sheets 25 and 28 are not aligned). Such an arrangement is readily apparent in FIG. 3, wherein the apertures 86 of the nonwoven sheet 28 are larger than the apertures 83 of the formed film topsheet 25. Such an arrangement provides the sanitary napkin 10 at least two beneficial properties: enhanced gush acquisition and enhanced wipe acquisition. Gush acquisition is enhanced in those areas where the apertures 83 of the topsheet 25 are aligned with the apertures 86 of the nonwoven wipe acquisition sheet 28. The aligned apertures 83 and 86 provide a direct route for exudates to flow from the body surface 26 of the topsheet 25 to the central absorbent materials of the napkin 10. Further, the apertures 83 and 86 themselves are able to contain a degree of fluid within their walls or boundaries until such fluid is absorbed. Wipe acquisition, which is the ability to pull liquid exudates from the wearer's skin into the absorbent material of the napkin 10, is enhanced in those areas where fiber bundles 89 of the nonwoven wipe acquisition sheet 28 are aligned such that the fiber bundles 89 are beneath the openings of the apertures 83 of the topsheet 25.

As just mentioned, wipe acquisition is critical in those regions where the topsheet 25 is in contact with exudates on the wearer's skin. In such areas, the sanitary napkin 10 is likely under compressive forces from the wearer's body. When such is the case, the fiber bundles 89 of the nonwoven wipe acquisition sheet 28 beneath the apertures 83 of the topsheet 25 are forced somewhat up into the apertures 83 of the topsheet 25, closer to the wearer's skin. Obviously, the spaces between the fiber bundles 89 and the walls of the apertures 83 or between the fibers of the fiber bundles 89 themselves will be less than the spaces which were between only the walls of the apertures 83. These spaces are capillaries. As is well known in the art, as capillary spaces are decreased, capillary or drawing action is increased. Thus, the capillary action in these apertures 83 where fiber bundles 89 are present is increased and the sanitary napkin 10 is better able to draw exudates from the wearer's skin into these capillaries and eventually into the central absorbent materials of the sanitary napkin 10.

Although all of the apertures 83 of the topsheet 25 are referenced by the numeral "83", for the following teaching purposes, specific reference is directed to the aperture of FIG. 3 specifically labeled and designated "83". The specific aperture 83 referenced is an example in which an aperture 83 of the topsheet 25 is aligned with an aperture 86 of the nonwoven wipe acquisition sheet 28. Theoretically, such an aperture is useful for gush acquisition since exudates have uninterrupted flow from the body surface 26 of the topsheet 25 to the central absorbent material (not shown). Next, attention is directed to the aperture 83 immediately to the right of the specific aperture 83 just referenced. As seen, this aperture 83 is superimposed over a fiber bundle 89 of the nonwoven wipe acquisition sheet 28. Theoretically, exudates that flow into the aperture 83 will enter the capillaries of the fiber bundle 89. The exudates will then either be pulled or absorbed into the central absorbent materials or wicked to intersecting fiber bundles 89, then wicked further to other intersecting fiber bundles 89, and so on, until the exudates are absorbed into a more laterally distant portion of the central absorbent materials. Hence, a large portion of the total absorbent capacity of the absorbent materials can be utilized.

As previously mentioned, the sanitary napkin 10 of the present invention has a liquid capacity great enough to absorb medium to high menstrual flows. Two capacities, which, depending on the size of the sanitary napkin may be the same, are determinable: test capacity and total capacity. Preferably, the napkin 10 of the present invention has a test capacity of at least about 8.0 grams, more preferably of at least about 15.0 grams, and most preferably of at least about 18.0 grams. Preferably, the napkin 10 of the present invention has a total capacity of at least about 20.0 grams, more preferably of at least about 30.0 grams, and most preferably of at least about 40.0 grams.

The test and total capacities of a sanitary napkin are determined as follows. Any panty adhesive release paper is removed from the napkin to be tested. To determine test capacity, a 4.75×14.0 centimeters portion of the sanitary napkin is cut from the portion of the sanitary napkin which would be centered under the vaginal orifice when the sanitary napkin is worn. Total capacity is determined using the entire napkin minus any release paper. The article is weighed to the nearest 0.1 gram. The article is then submerged in a beaker of sterile saline (obtainable from the Baxter Travenol Company of Deerfield, Ill.), such that the article is totally submerged and is not bent or otherwise twisted or folded. The article is submerged for 10 minutes. The article is removed from the saline and suspended for two minutes in a vertical position to allow the saline to drain out of the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the test or total capacity of the article, whichever the case may be.

The central absorbent width 63 of absorbent material of the sanitary napkin 10 of the present invention is an important parameter. The term "central absorbent width" refers to a specific area of the sanitary napkin 10 determinable as follows, reference being had to FIG. 5. A point 64 on the sanitary napkin 10 which is disposed beneath the center of the vaginal orifice, when worn, is located. A plane 65 parallel to the lateral centerline 61 and 3.75 centimeters forward from the point 64 in the direction of the wearer's mons pubis is located. Another plane 66 parallel to the lateral centerline 61 and 5.0 centimeters rearward from the point 64 in the direction of the wearer's buttocks is also located. The greatest flat-out, uncompressed, unmanipulated, lateral width of absorbent material of the sanitary napkin 10 between the planes 65 and 66 is the central absorbent width 63 of the sanitary napkin 10. It matters not whether the absorbent material is a single sheet, overlapping sheets, staggered sheets, etc., and it matters not whether the absorbent material is a nonwoven sheet, an absorbent topsheet, an example, a sanitary napkin 10 of the present invention might have a wipe acquisition sheet 28 or a wet-laid tissue 31 having a width of about 7.75 centimeters and an absorbent core 34 having a width of about 3.8 centimeters. Thus, in this example, the sanitary napkin 10 has a central absorbent width 63 of 7.75 centimeters.

The sanitary napkin 10 of the present invention must have a central absorbent width 63 of at least about 6.5 centimeters, more preferably of at least about 7.0 centimeters, more preferably of at least about 7.75 centimeters, and most preferably of at least about 9.0 centimeters. The central absorbent width 63 of the sanitary napkin 10 of the present invention is believed important for the following reason. As stated previously, the sanitary napkin 10 of the present invention relies more on the lateral distribution of exudates over or through a relatively large surface area of the absorbent core 34 rather than on a high degree of vertical absorption common to many prior art sanitary napkins. Therefore, because exudates which are distributed onto the topsheet 25 may not be quickly absorbed before they migrate across the topsheet 25, it is important to contain such exudates pending absorption. The specified central absorbent width 63 of the sanitary napkin 10 of the present invention has been determined based on the width of a flexible napkin which will cup around the labia in the region of the vaginal orifice such that at least the edges of the absorbent material are positioned in the uppermost part of the wearer's legs at the crotch. Thus, the sanitary napkin 10 and the absorbent material may be cupped shaped in the surrounding regions of the vaginal orifice and exudates deposited thereon will be contained until absorbed.

Because of the flexibility requirements of the sanitary napkins 10 of the present invention, it is likely that the sanitary napkins 10 of the present invention will be relatively thin. It is preferred to keep the sanitary napkins 10 of the present invention thin so that they will have a low wearing awareness and also to keep them as unobtrusive as possible. The sanitary napkin 10 shown in FIGS. 1 and 2 has a caliper of about 1.9 millimeters.

The caliper of a sanitary napkin 10 is determined by the following test.

A comparator gauge, and specifically the Ames, Model 130 with dial indicator Model 482, available from the B.C. Ames, Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparator foot is raised and the napkin, with any panty adhesive release paper being removed, is placed garment surface down on the base plate. The napkin is positioned on the base plate so that when the foot is lowered it is in the center of the napkin. Try to smooth out or avoid any wrinkles in the napkin. Gently lower the foot onto the napkin. Determine the napkin caliper by reading the comparator dial 30 seconds after the foot comes in contact with the napkin. Repeat the measurement 3.0 centimeters from each of the ends of the absorbent material along the longitudinal centerline 58 of the napkin. The average of the three readings is the caliper of the sanitary napkin. Preferably, the sanitary napkins 10 of the present invention have a caliper of less than about 2.6 millimeters, more preferably less than about 2.2 millimeters, and most preferably less than about 2.0 millimeters.

An alternative embodiment of a sanitary napkin 10 of the present invention is shown in FIG. 4. In this embodiment, the sanitary napkin 10 has two flaps 70 each of which are adjacent to and extend laterally from a side edge 55 of the absorbent core 34. The flaps 70 are configured to drape over the edges of the wearer's panties in the crotch region so that the flaps 70 are disposed between the edges of the wearer's panties and the wearer's thighs. The flaps 70 serve at least two purposes. First, the flaps 70 help serve to prevent soiling of the wearer's body and panties by menstrual fluid. Second, the flaps 70 are preferably provided with attachment means 71 on their garment surface 17 so that the flaps 70 can be folded back under the panty and attached to the garment facing side of the panty. In this way, the flaps 70 serve to keep the napkin 10 properly positioned in the panty. A preferred attachment means 71 is a pressure-sensitive adhesive, as is well known in the art. Alternatively, the flaps 70 may be attached to each other on the underside of the panty by the attachment means 71 without being affixed to the panty.

In the preferred embodiment shown, the flaps 70 are comprised of topsheet 25, tissue 31, and barrier sheet 16. Further, in the embodiment shown, the flaps 70 are unitary with the laminae of the napkin 10. In other words, the topsheet 25, tissue 31 and barrier sheet 16 simply extend laterally beyond the core 34 to form the flaps 70. However, the flaps 70 need not be unitary with the napkin 10 but can be separate elements which are affixed to the napkin 10. Further, the flaps 70 can be comprised of a single substrate or other laminae configurations. It is recommended, however, that the flaps 70 have a liquid impervious barrier sheet 16. The barrier sheet 16 prevents exudates which reach the flaps 70 from soiling the edges of the wearer's panties. Further, it is preferable that the flaps 70 be provided with an absorbent layer, at least to a point beyond the edges of the wearer's panties. Theoretically, only a relatively small amount of menses should reach the flaps 70, therefore, only a relatively small amount of absorbent material is desirable in the flaps 70. However, at least some absorbent material is recommended in order to prevent any exudates that reach the flaps 70 from being able to flow further to unprotected areas. The absorbent material may be a tissue, such as the tissue 31, or an extension of the absorbent core 34, such as the WATER-LOCK L-535. However, the absorbent material in the flaps 70 should be relatively highly flexible. A number of sanitary napkins having flaps suitable or adaptable for use with the sanitary napkins 10 of the present invention are known. Such flaps are disclosed in U.S. Pat. No. 4,687,478, entitled "Shaped Sanitary Napkin With Flaps", which patent issued to Van Tilburg on Aug. 18, 1987, U.S. Pat. No. 4,608,047, entitled "Sanitary Napkin Attachment Means", which patent issued to Mattingly on Aug. 26, 1986, U.S. Pat. No. 4,589,876, entitled "Sanitary Napkin", which patent issued to Van Tilburg on May 20, 1986, and U.S. Pat. No. 4,285,343, entitled "Sanitary Napkin", which patent issued to McNair on Aug. 25, 1981, all of which patents are incorporated herein by reference.

For illustration purposes, the central absorbent width 63 of the napkin 10 shown in FIG. 4 would extend laterally from the outer edge 32 of the tissue 31 in the one flap 70 to the outer edge 32 of the tissue 31 in the other flap 70.

Another alternative embodiment of a sanitary napkin 10 of the present invention is shown in FIG. 5. Like the napkin 10 shown in FIG. 4, this napkin 10 also has flaps 70, only of a different configuration. In this embodiment, the flaps 70 are comprised only of the topsheet 25 and the barrier sheet 55.

For illustration purposes, the central absorbent width 63 of the napkin 10 shown in FIG. 5 would extend laterally from one outer edge 32 of the tissue 31 to the other outer edge 32 of the tissue 31.

While particular embodiments of the present invention have been illustrated and described, it would be obvious to those skilled in the art that various other changes and modifications can be made without departing from the spirit and scope of the invention.

What is claimed is:

1. A sanitary napkin comprising:
   a liquid permeable topsheet;
   a liquid impermeable barrier sheet;
   an absorbent core intermediate said topsheet and said barrier sheet;
   said sanitary napkin having a test capacity of at least 8.0 grams, a total capacity of at least about 20.0 grams, an absorbent portion with a flexure resistance less than 250.0 grams, and a caliper less than 2.6 millimeters.

2. A sanitary napkin according to claim 1 having a total capacity of at least 30.0 grams.

3. A sanitary napkin according to claim 2 having a test capacity of at least 15.0 grams.

4. A sanitary napkin according to claim 2 having a total capacity of at least 40.0 grams.

5. A sanitary napkin according to claim 4 having a test capacity of at least 18.0 grams.

6. A sanitary napkin according to claim 1 having a flexure resistance less than 175.0 grams.

7. A sanitary napkin according to claim 6 having a flexure resistance less than 130.0 grams.

* * * * *